(12) United States Patent
Freda et al.

(10) Patent No.: US 6,217,592 B1
(45) Date of Patent: Apr. 17, 2001

(54) LAPROSCOPIC INSTRUMENT FOR SUTURING TISSUE

(76) Inventors: Vincent Freda, 161 Ft. Washington Ave., New York, NY (US) 10032; Richard V. Mazzola, 43 Spring Valley Rd., Blairstown/Hardwich, NJ (US) 07825

(*) Notice: Subject to any disclaimer, the term of this patent is extended or adjusted under 35 U.S.C. 154(b) by 0 days.

(21) Appl. No.: 09/413,207

(22) Filed: Oct. 5, 1999

Related U.S. Application Data

(60) Provisional application No. 60/103,296, filed on Oct. 6, 1998.

(51) Int. Cl.[7] .................................................. A61B 17/04
(52) U.S. Cl. ............................................ 606/145; 606/144
(58) Field of Search ................................ 606/144–148

(56) References Cited

U.S. PATENT DOCUMENTS

| | | | |
|---|---|---|---|
| 4,596,249 | * 6/1986 | Freda et al. | 606/145 |
| 5,454,823 | * 10/1995 | Richardson et al. | 606/148 |
| 5,690,652 | * 11/1997 | Wurster et al. | 606/144 |
| 5,843,099 | * 12/1998 | Nichols et al. | 606/144 |
| 5,908,428 | * 6/1999 | Scirica et al. | 606/139 |
| 5,980,538 | * 11/1999 | Fuchs et al. | 606/145 |

\* cited by examiner

*Primary Examiner*—Gary Jackson
(74) *Attorney, Agent, or Firm*—Evelyn M. Sommer

(57) ABSTRACT

A laproscopic instrument for setting sutures, particularly suitable for use in situations where access to the tissue to be sutured is difficult. The implement includes a pair of hinged arms, each having a handle portion and a jaw portion. The tip of one jaw has a notch or opening through which the hook may pass. A series of guides and openings position the sututre above the opening for engagement by the hook. When the jaws are closed about the tissue, the hook will pass through the tissue and the suture will ride around the hook. The suture will be engaged by the hook and upon opening the jaws, the hook will pull a loop of suture through the tissue. The suture is fixed in the usual manner.

5 Claims, 3 Drawing Sheets

LAPROSCOPIC INSTRUMENT FOR SUTURING TISSUE

RELATED U.S. APPLICATION DATA

This is based on a provisional Ser. No. 60/103,296 filed on Oct. 6, 1998.

BACKGROUND OF THE INVENTION

The invention is an instrument for setting a suture in laproscopic surgery. In Laproscopic surgery there is a need to sew up by sutures (blood vessels and tissue within the body) by action outside the body. The "action" is done by instruments inserted within the body via one or more trocars that are maintained in a fixed position in the body throughout the surgery.

Presently the setting or tying of a suture generally involves a pair of separate instruments, a needle holder and a threaded needle, and each is inserted into the body cavity through an abdominal trocar that typically are between which are narrow 5 mm and 10 mm's wide. Because there are two separate instruments to be controlled, the setting of a suture is relatively difficult to control. Moreover in some instances when the two are inserted together, the holder holding the needle, then is a risk that the two become separated within the cavity, which makes the suturing difficult.

SUMMARY OF THE INVENTION

To simplify the suturing process, the invention is a suturing instrument that composes an integral instrument in the sense that the component parts one locked together and not physically separable while in the body. As such change is need for only a single trocar for introduction of the instrument and control is facilitated by the need to maneuver only the instrument.

The present invention is a modification of the suture instrument described in U.S. Pat. No. 4,596,249 that issued on Jun. 24, 1986 to Vincent J. Freda and Henry Puchalski and is unassigned.

DETAILED DESCRIPTION OF THE INVENTION

Figure 1:
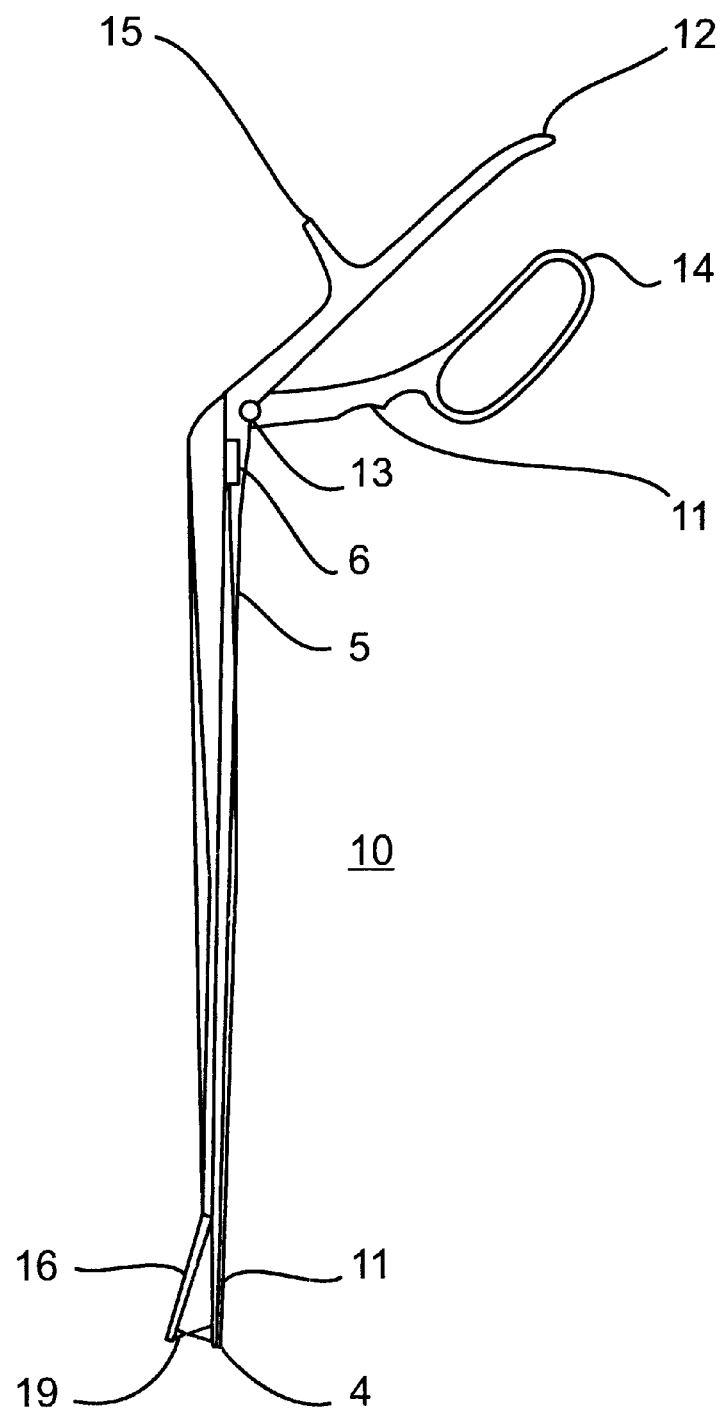
FIG. 1 is a plan view of an illustrative embodiment of the invention in an essentially closed position.

With reference now to the drawing FIG. 1 composes two arms 11 and 12 that are hinged together at the pivot point 13 as in a pair of scissors. Arm 11 included at the end to be external to the body during the procedure includes a handle loop 14 for controlling the opening and closing of the jaw ends of the arms that will be within the body during the procedure.

Figure 2:
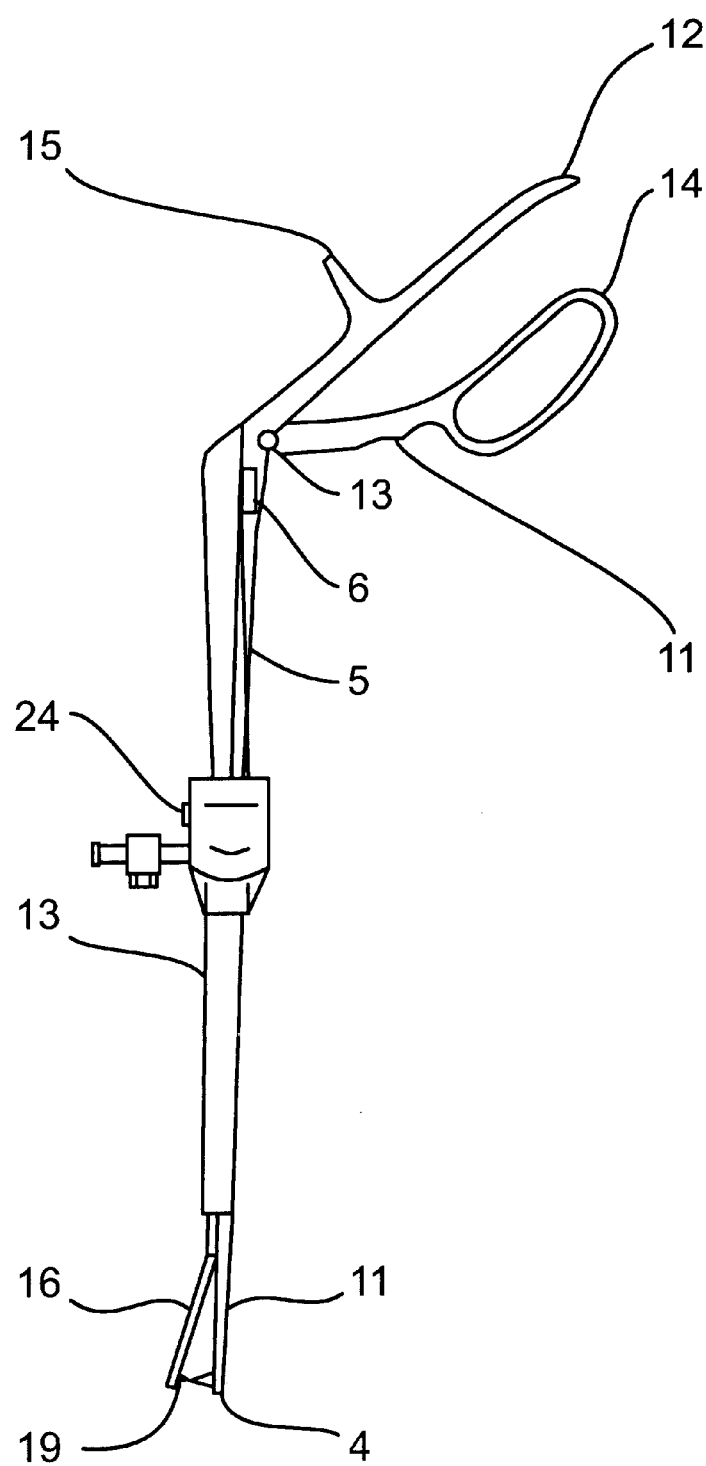
FIG. 2 is a similar view of which there has been the trocar that would be inserted in the abdominal wall of the body to provide the opening through which the instrument is inserted in and out of the body to do the suturing.
Figure 5:
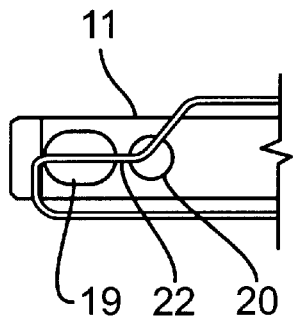
FIG. 5 is a top view of the upperside of the end portion of the lower jaw Part B.
Figure 4:
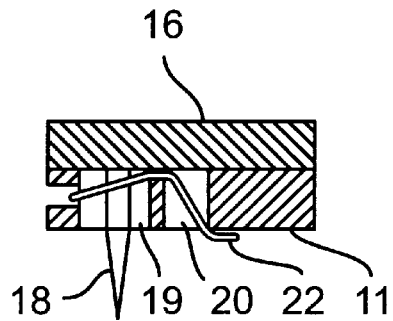
FIG. 4 is a cross section of end positions of the instrument showing the relationships of the critical parts of the instrument in the closed position.
Figure 3:
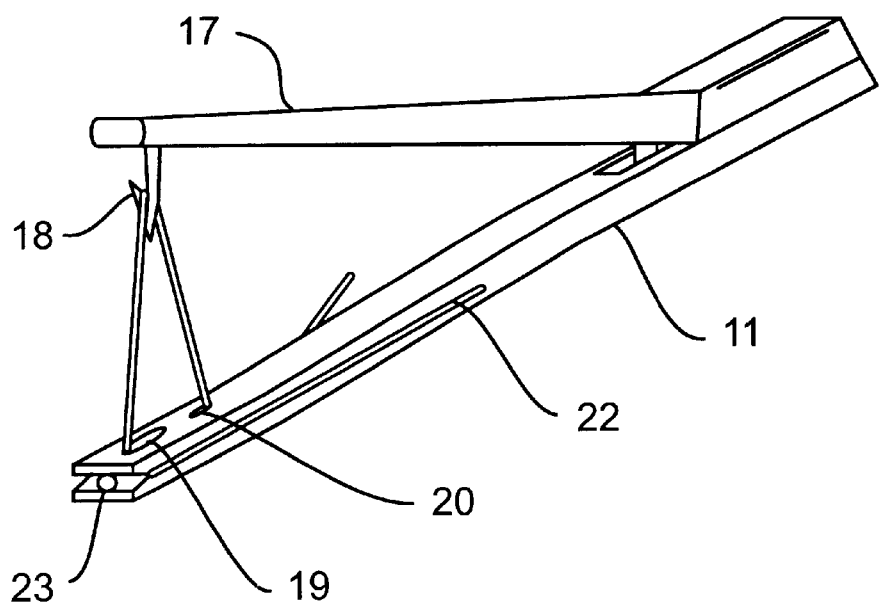
FIG. 3 is a perspective view of the jaw ends of the instrument in an open position after these have engaged the thread using for the suturing.

In FIG. 2 there is shown the trocar 24 that is inserted in the abdominal wall of the body to remain fixed during the procedure and through which the surgical instrument is inserted into the abdominal cavity. Arm 12 is optimally provided with a projection 15 to promote an improved grip of the instrument. As with a pair of scissors, the opening and closing of the ends of the arms external to the body promote the closing and opening of the jaw ends of the arms that are internal in the body. Each of FIGS. 1 and 2 show the instrument with the jaws closed. FIG. 3 shows the instrument with the jaw open. As seen in FIG. 3, the arm 11 included at its jaw end with a hinged portion 17 that opens and closes with respect to the lower jaw, which is not hinged. The hinged portion will be completely within the body when the instrument is properly inserted in the body, and in the closed position can be readily inserted into and withdrawn out of the body by way of the trocar.

As best seen in FIG. 3, the end of the hinged jaw 17 is provided with a hook 18 that is used to engage the thread 22 that is used for the suture.

The lower arm 11 at its jaw end has three holes. The first 23 is at the top of the jaw, the second is a larger hole 19 which extends through the jaw and the third is a smaller hole 20 next to the larger hole 19 which also extends through the lower jaw. The suture 22 is initially inserted into hole 23 and extends out and upwards through hole 19 and then the suture is inserted downward through hole 20 and exits from the bottom of the jaw. The thread 22 extends so the length of the instrument is secure with a clamp similar to 6 shown in FIG. 1 on the right side of the instrument, but is not disclosed in the diagram. That half of the suture which remains at hole 23 is extended alongside of the left side of the instrument and is secured with clamp 6 shown in FIG. 1.

Preferably a guide or clamps not shown is provided along the far side of the arm for the thread. Similarly, the thread 22 runs a guide or clamps (not shown) on the near side of the arm 11. The two positions of the thread pass through the trocar to the outside of the body where the ends can be tied together.

The hook 18 and the opening 19 are so aligned that when the jaws are closed the hook will loop into the opening 19 sufficiently to engage the jaws are reopened the thread will be lifted up as shown in FIG. 3.

When a suture is to be placed around a blood vessel or tissue within the abdomen the thread instrument with its jaws closed is inserted in the trocar, and once inside the abdomen, the jaws are opened. The ends of the suture are released from the clamps and held by the surgeon in one hand. After the instrument is positioned approximately for suturing, the jaws of the instrument are closed appropriately enveloping the blood vessel or tissue to be sutured in the usual fashion. In the closing, the hook engages the thread as it passes into the larger opening 19. Then, the instrument is removed via the trocar the instrument is pulled away from the blood vessel or tissue being sutured, the jaws are closed and the instrument in the closed position in pulled out of the body cavity by way of the trocar. In the process, the ends of the thread 22 are pulled outside of the body and then can be tied together to complete the suturing.

It will be understood that the invention may be embodied in other forms without departing from such principles and the fair scope of the invention.

What is claimed is:

1. An implement for setting a suture in tissue said implement comprising:

a first and second hinged arms, each arm defining a proximal handle and a distal jaw portion;

said jaw portion of said first arm having a first and second bores perpendicularly therethrough, said jaw portion of said first arm having an longitudinal bore from the distal end of said first arm which extends into said first bore;

said jaw portion of said second arm having a hook constructed and arranged to pierce tissue and being sized to pass through said first bore of said jaw portion of said first arm when the jaws are closed;

suturing positioning means disposed in said first arm said positioning means disposing a portion of said suture proximate said opening in said jaw portion of said first arm, said elongated bore and said first bore and said second bore of said first area adapted and constructed to act as guides for suture thread;

said hook engaging a portion of said suture disposed proximate said first bore when said jaws are closed, upon the opening of said jaws said hook retracting a loop of said suture through the opening pierced in said tissue.

2. The implement as claimed in claim 1 wherein said handle portion of at least one of said first and second arm include means for fixing one end of said suture thereto.

3. The implement as claimed in claim 2 wherein said means for fixing cover end of said suture includes a flexible leaf clamp under which a portion of said suture may be wedged.

4. The implement of claim 1 wherein the first and second bores are connected by a groove along the jaw portion.

5. The implement of claim 1 wherein the distal end of said first arm has a notch for guiding said suture.

* * * * *